United States Patent [19]

Srivastava et al.

[11] Patent Number: 4,764,598

[45] Date of Patent: Aug. 16, 1988

[54] PRECURSORS TO RADIOPHARMACEUTICAL AGENTS FOR TISSUE IMAGING

[75] Inventors: Prem C. Srivastava; Furn F. Knapp, Jr., both of Oak Ridge, Tenn.

[73] Assignee: The United States of America as represented by the Department of Energy, Washington, D.C.

[21] Appl. No.: 25,703

[22] Filed: Mar. 13, 1987

Related U.S. Application Data

[62] Division of Ser. No. 768,385, Aug. 22, 1985.

[51] Int. Cl.[4] .................. C07C 115/00; C09B 56/20
[52] U.S. Cl. .................. 534/551; 546/316; 424/1.1
[58] Field of Search .................. 534/551; 546/316; 424/1.1

[56] References Cited

U.S. PATENT DOCUMENTS 3,162,571  12/1964  Adams et al. .................. 534/551 X
3,741,951   6/1973  Hess et al. .................. 534/551
4,479,932  10/1984  Bodor .................. 546/316 X
4,514,408   4/1985  Nisato et al. .................. 546/316 X

FOREIGN PATENT DOCUMENTS

83/03968  11/1983  PCT Int'l Appl. .................. 546/316

OTHER PUBLICATIONS

Tedjamulia, M. L. et al, "Brain-Specific Delivery of Radioiodinated Amines", J. Med. Chem., Nov. 1985, pp. 1574–1580.

Primary Examiner—John F. Terapane
Assistant Examiner—John S. Maples
Attorney, Agent, or Firm—Katherine P. Lovingood; Stephen D. Hamel; Judson R. Hightower

[57] ABSTRACT

A class of radiolabeled compounds to be used in tissue imaging that exhibits rapid brain uptake, good brain:blood radioactivity ratios, and long retention times. The imaging agents are more specifically radioiodinated aromatic amines attached to dihydropyridine carriers, that exhibit heart as well as brain specificity. In addition to the radiolabeled compounds, classes of compounds are also described that are used as precursors and intermediates in the preparation of the imaging agents.

6 Claims, 2 Drawing Sheets

PRECURSORS TO RADIOPHARMACEUTICAL AGENTS FOR TISSUE IMAGING

This invention was developed pursuant to a contract with the U.S. Department of Energy.

This is a division of application Ser. No. 768,385, filed Aug. 22, 1985.

BACKGROUND OF THE INVENTION

This invention relates to a radioiodinated aromatic amine attached to dihydropyridine carriers that show tissue specificity and are potentially useful as imaging agents. Although this radiopharmaceutical was developed for application as a brain imaging agent, it also exhibits specificity in other tissues, most notably the heart.

The ability to measure cerebral blood flow is useful in the gathering of clinical information for the identification and evaluation of brain lesions. The technology recently developed to make such measurements involves the use of a radiopharmaceutical agent in conjunction with single photon emission computerized tomography (SPECT). One approach in the development of an appropriate radiopharmaceutical agent is to first select a suitable radioisotope and then attach that radioisotope to a carrier that can cross the intact blood-brain barrier. The complexity of the problem becomes apparent when one considers the many radioisotopes that could possibly be chosen such as technetium, fluorine, thallium, and iodine to name a few, as well as possible carriers such as amphetamines, barbiturates, or other compounds that exhibit central nervous system activity.

The most recent work in the area of brain imaging using SPECT has involved the use of the radioisotope iodine-123 which has excellent radionuclidic and chemical properties for use in diagnostic radiopharmaceuticals. The emission of abundant (84%) 159 keV gamma photons allows the use of Anger-type cameras which are available in all nuclear medicine clinics. This radionuclide, iodine-123, has been used in conjunction with fatty acids, human serum albumin and triglycerides to develop radiopharmaceutical agents.

Experimental work has continued to arrive at a suitable carrier for transporting the radionuclide. One consideration, and perhaps the most important, is the ability of a molecule to pass the blood-brain barrier. This ability is a function of its partition coefficient between lipid and water. Lypophilic organic compounds cross the intact blood-brain barrier and mimic regional blood flow which is a necessary characteristic for the radiopharmaceutical agents under consideration. One known carrier is in the form of an amphetamine which has been reported and shows good retention in the brain. Previous work has also involved an attempt at using radiolabeled barbiturates. Although barbiturates exhibited good brain uptake, the transport was reversible with the carrier leaving the brain as rapidly as it entered resulting in washout and rapid clearance of the isotope from the brain. There was also exhibited a low brain:blood ratio resulting in high background radioactivity. The barbiturates also have the disadvantage, which can be attributed to the amphetamines as well, of having an addictive effect on the central nervous system. Recently a dihydropyridine derivative of a quaternary salt that can be delivered to the brain was reported by Bodor et al. The derivative was developed for chemotherapeutic treatment of brain disease, but offers possible applications in brain imaging technology with further development. In view of the problems in this area there is a need for an improved radiopharmaceutical agent that can enter the brain and be used in conjunction with known imaging methods to detect certain occurrences within the brain.

SUMMARY OF THE INVENTION

In view of the above-mentioned needs, it is an object of this invention to provide a class of radiopharmaceuticals appropriate for tissue imaging.

Another object is to provide a class of radiopharmaceuticals useful in the detection and evaluation of brain disease.

It is also an object of this invention to develop radiopharmaceuticals that can be manufactured simply and quickly.

It is a further object of this invention to provide radiopharmaceuticals that exhibit rapid and pronounced brain uptake, significant brain:blood ratios, and which are retained in the brain for a sufficient length of time for radioimages to be recorded.

Another object of the invention is to provide radiopharmaceuticals that have no addictive side effects.

Another object of this invention is to provide non-radiolabeled compounds that are used as starting materials for the production of radiolabeled pharmaceuticals.

It is also an object of this invention to provide a compound that is useful as a precursor in the preparation of site-specific pharmaceuticals.

Additional objects of the invention will be set forth in part in the description which follows and will become apparent to those skilled in the art. The objects and advantages of the invention may be realized and attained by means of instrumentalities and combinations particularly pointed out in the description and the appended claims.

The invention is a class of compounds having a hydrogenated heterocyclic moiety wherein the hetero member of the ring is nitrogen. It is hydrogenated and lypophilic but can be oxidized to a quaternary form, and has a carbonyl group attached to the heterocyclic ring. The heterocyclic moiety is coupled at the carbonyl carbon with a radiolabeled aromatic or aromatic alkyl amine. In the preferred embodiment, the heterocyclic moiety is a dihydropyridine but can be a quinoline, nicotine, pyrimidine or other similar hydrogenated moiety. The compounds of this class are useful as tissue imaging agents.

The invention is also a saline solution or other suitable administering medium containing any of the compounds of the above-identified class in amounts sufficient to produce a distinct tissue image using known radioimaging techniques.

The invention is also a class of compounds characterized by an unsaturated heterocyclic moiety, wherein the hetero member of the ring is nitrogen, that can be oxidized or reduced to a quaternary or hydrogenated lypophilic form having a carbonyl group attached to the heterocyclic ring. This moiety is coupled at the carbonyl carbon with an organic moiety that activates the carbonyl carbon to make it sufficiently reactive for a nucleophilic attack by an amine. In the preferred embodiment, the organic moiety that activates the carbonyl carbon is N-hydroxysuccinimide but could also be p-nitrophenol or another active phenol. The compounds of this class are useful as precursors for site-specific pharmaceuticals.

Although the radiolabeled compounds of this invention are the ones to be used for tissue imaging, they may not be suitable for long-term storage or transportation. Therefore, the invention is also a class of compounds characterized by a quaternary heterocyclic moiety, wherein the hetero member of the ring is nitrogen, that can be reduced to a hydrogenated lypophilic form, having a carbonyl group attached to the heterocyclic ring. This moiety is coupled at the carbonyl carbon with an aromatic or aromatic alkyl amine, the amine having attached to the aromatic ring a moiety that is readily replaced by a radiohalide. The attached moiety could be a substituted triazene compound, mercuric acetate, a boron moiety or other similar moiety readily replaced by a halide. The compounds of this class can be used as starting materials from which the radiolabeled imaging agents are made, and since they are not subject to radioactive decay they can be kept indefinitely.

The invention is also a class of compounds characterized by a quaternary heterocyclic moiety, wherein the hetero member of the ring is nitrogen, that can be reduced to a hydrogenated lypophilic form, naving a carbonyl group attached to the heterocyclic ring. This moiety is coupled at the carbonyl carbon with a radiolabeled aromatic or aromatic alkyl amine. The compounds of this class are useful as starting materials for making the lypophilic radiolabeled compounds. Although they are subjected to radioactive decay, they are still more stable than their hydrogenated products, which are easily oxidized, and thus are more suitable for storage and transportation.

The compounds of this invention are significant improvements in this field of technology. The preferred imaging agents labeled with I-123 are very appropriate for scanning with SPECT due to iodine's abundant gamma photon emission. The carrier dihydrogenated pyridine moiety crosses the blood-brain barrier and is trapped, thereby retaining the radioactive iodine in the brain while permitting the radioactive iodine attached to the nondihydrogenated pyridines to be washed from the system. This "trapping" will be further explained in the detailed description of the preferred embodiment of this application. The iodinated carrier exhibits rapid uptake and long retention in the brain and exhibits significant brain:blood ratios and has the benefit of no addictive side effects. The precursor is promising for preparation of other site-specific pharmaceuticals because the carbon of the carbonyl group is activated and readily undergoes coupling. The starting materials for the preparation of the imaging agents are not only useful as starting materials (or intermediates) but also are more stable than their imaging agent products and thus have the advantage of longer life for storage and transportation purposes. All compounds possess the advantage of being fast and easy to prepare.

DESCRIPTION OF THE DRAWING

FIG. 1, comprising two pages designated

DETAILED DESCRIPTION OF THE PREFERRED EMBODIMENT

In brain imaging using SPECT and other computerized and electronic photographic techniques it is necessary to provide radioactive decay at the tissue specific site where imaging is desired. To accomplish this one requirement is a radioactive component, and a second requirement is a means of transporting the radioactive component to the site. In the preferred embodiment of this invention the radioactive component is a radioiodinated aromatic amine and the transporting means is a dihydropyridine carrier.

The dihydropyridine carrier is derived from a unique class of heterocyclic quaternary compounds represented by the general formula [Q+], that has recently been reported by Bodor et al. Accordingly, in this invention the quaternary form of the compound is not lypophilic and is therefore impermeable to the blood-brain barrier. However, it is chemically reduced under mild conditions to provide the lipid soluble hydrogenated form [HQR] where R represents the radiolabeled constituent. When administered intravenously as the [HQR] form, the compound is rapidly distributed throughout the body. The reduced form [HQR] of the compound becomes rapidly oxidized to [Q+R] within most body tissues. Since [Q+R] is hydrophilic and ionic it will be rapidly eliminated from these tissues. Since the [HQR] form is lipid soluble, the compound is quickly transported across the blood-brain barrier. The oxidation of [HQR] in the brain, however, will restore the compound to the original quaternary form [Q+R] which is not lipid soluble and can no longer pass through the blood-brain barrier. This results in a unique "trapping" of the compound in the brain. This unique property of selective trapping of radiopharmaceuticals in the brain provides high brain uptake, very low retention in the blood and other body tissues resulting in high brain:blood ratios required for optimal brain imaging. Two radioiodinated dihydropyridines, a precursor for both and a number of useful intermediates have been developed and are described in this application. It is believed that other lypophilic heterocyclic compounds, similar to dihydropyridine, which can be oxidized to quaternary forms would behave in a similar manner.

Iodine-125 was used in the experimental testing of rats but iodine-123 would be the radioisotope most likely to be used for human applications. Other radioactive halides could also be used. For instance iodine-131 is a possibility, as are bromine-75 and -76, (and perhaps -82 with improvements in present technology). However, the bromine isotopes are positrons and would require an imaging technique other than SPECT. Fluorine-18 could be used if fluorinated amines become available.

Figure 1A:
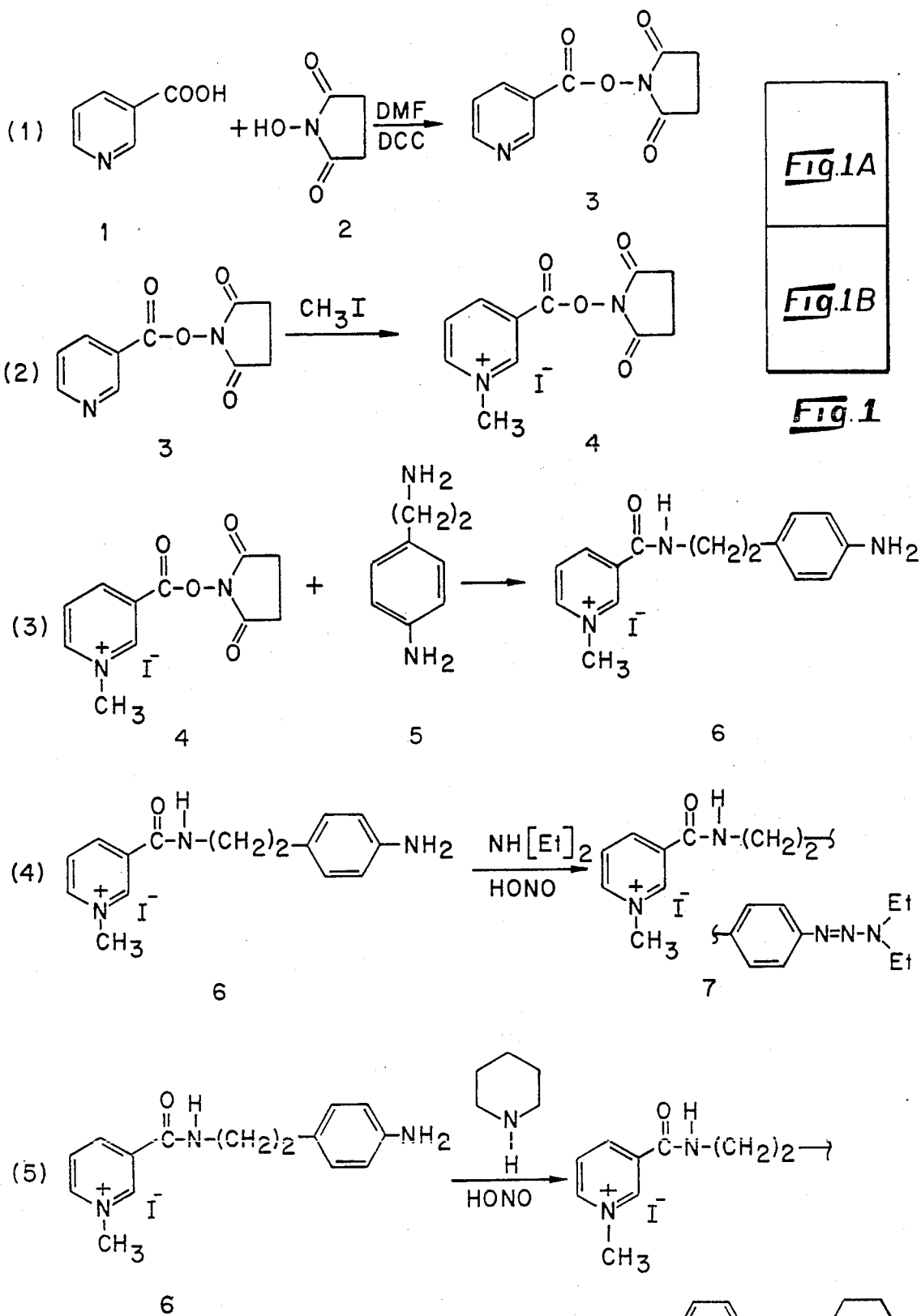
FIG. 1A and FIG. 1B, illustrates by way of chemical equations the steps of the reactions given in the Example.
Figure 1A:
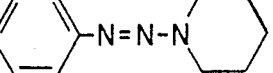
Figure 1B:
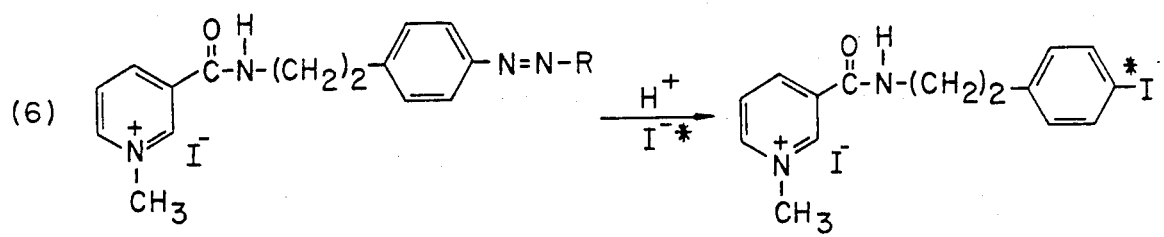
Figure 1B:
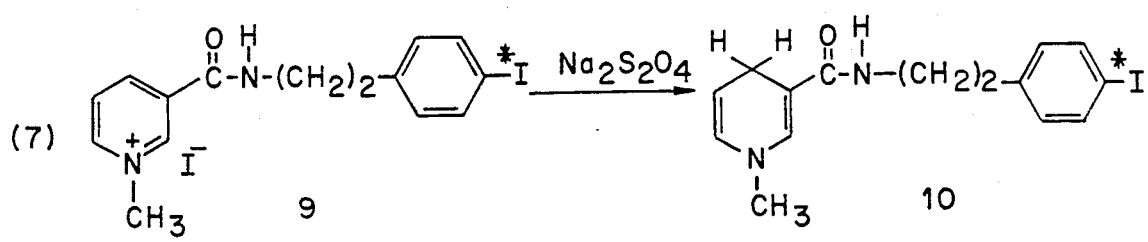
Figure 1B:
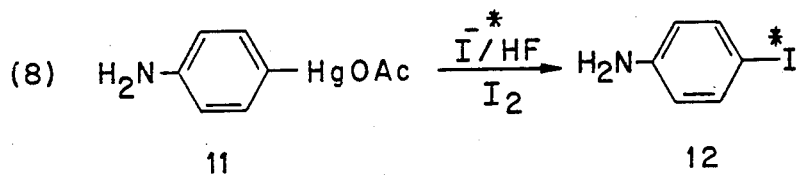
Figure 1B:
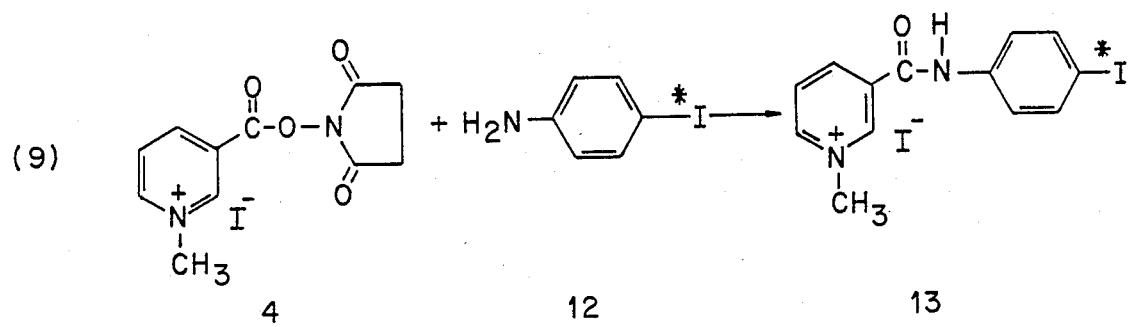
Figure 1B:
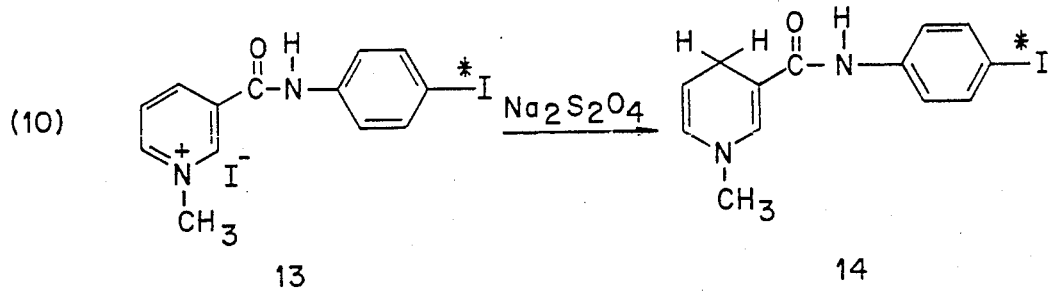

FIG. 1 sets forth in equations the steps of the reaction described in the Example. Although the Example using I-123 is the preferred embodiment, certain constituents can be substituted. In step 2, $CH_3I$ is more generally defined as RX where R is an alkyl or aryl group and X is an anion. In compound 5, $CH_2$ is more generally described as $R_1$ where $R_1$ is an alkyl group. In steps 4 and 5, $NH[Et]_2$ and

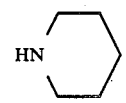

are more generally described as $HN[R]_2$ where R is an alkyl or aryl group. In step 6 and step 8, $I^{-*}$ can be other halide isotopes previously mentioned such as I-123, I-125, I-131, Br-75, Br-76, Br-82 and F-18.

The following methods were employed in the procedures described in the Example contained in this application. All chemicals and solvents were analytical grade and were used without further purification. The petroleum ether had a boiling range of 30°–60° C. The iodine-125 was purchased from New England Nuclear, Inc., (North Billierica, Mass.). 4-Aminophenyl mercuric acetate was purchased from Aldrich Chemical Company, Milwaukee, Wis. The melting points (mp) were determined in capillary tubes using Buchi SP apparatus and were uncorrected. The thin-layer chromatographic analyses (TLC) were performed using 250 μm, thick layers of silica gel G PF-254 coated on glass plates (ANALTECH, Inc.). The proton nuclear magnetic resonance spectra (NMR) were obtained at 60 MHz with a Varian 360 L instrument. Samples (30–40 mg) were dissolved in the solvents indicated and the resonances (ppm) were reported downfield ($\delta$) from the internal tetramethylsilane standard. The presence of exchangeable protons was confirmed by the addition of $D_2O$ and reintegration. The term para (p) and 4 have been used interchangeably for the numbering of the phenyl ring carbon.

EXAMPLE

FIG. 1 illustrates by way of chemical equations the steps of the procedure for preparing compounds 3, 10, and 14. Step 1 was conducted as follows: Dicyclohexylcarbodimide (DCC, 45.5 g, 220 mmol) was added to a solution of pyridine-3-carboxylic acid (1, 25.0 g, 200 mmol) and N-hydroxysuccinimide (2, 23.0 g, 250 mmol) in dimethylformamide (DMF) (500 mL). The reaction mixture which became slightly warm (~45° C.) during the addition of DCC was allowed to stir at room temperature for 48 h. Glacial acetic acid (4 mL) was added to the reaction mixture to decompose the excess of DCC. After stirring at room temperature for an additional hour, the white precipitate of dicyclohexylurea was removed by filtration. The filtrate was evaporated in vacuo to yield a pale yellow product which was crystallized from ethyl acetate to give N-succinimidyl-3-pyridinecarbonxylate (3) as white crystals: yield 75% (33.0 g), mp 138°–139° C.

In step 2, a solution of 3 (9.0 g, 41 mmol) and methyl iodide (11.6 g, 5.1 mL, 82 mmol) in anhydrous acetone (40 mL) was heated at 45° C. for 7 h in a flask equipped with an efficient condenser. A pale yellow colored product separated from the solution. The product was collected by filtration, washed thoroughly with acetone, and dried to yield (11.6 g, 78%) N-succinimidyl (1-methylpyridinium iodide)-3-carboxylate (4) as pale yellow crystals: mp 222°–223° C.

In step 3, a solution of p-aminophenylethylamine (5, 3.2 g, 23 mmol) in DMF (5 mL) was added slowly to a solution of compound 4 (7.8 g, 22 mmol) in DMF (25 mL) placed in a round bottom flask. The reaction mixture was stirred at room temperature for 8 h. The DMF was evaporated in vacuo to give a yellow solid which was crystallized from methanol to yield (6.8 g, 81%) pale yellow crystals of 1-methyl-3-[N-[β-(4-aminophenyl)ethyl]carbamoyl]pyridinium iodide (6).

In step 4, 1-methyl-3-[N[β-[p-(1-3,3-diethyl)triazen-1-ylphenyl]ethyl]-carbamoyl]pyridinium iodide (7) was prepared from compound 6 (730 mg, 1.9 mmol) in a manner similar to that described below for 8 in step 5, except that diethylamine (150 mg, 2.05 mmol) was used instead of pipiridine. Crystallization from chloroform and hexane gave 7 as orange crystals: mp 162°–163° C.

In step 5, a solution of 6 (450 mg, 1.17 mmol) in hydrofluoric acid (48% solution, 54 mg 1.29 mmol) was cooled (0° C.) in an icemethanol bath. A solution of sodium nitrite (111 mg, 1.30 mmol) in water (2 mL) was added dropwise while maintaining the reaction temperature at 0±4° C. A cold solution of pipiridine (106.4 mg, 1.25 mmol) and potassium carbonate (219 mg, 1.58 mmol) in water (3.5 mL) was added. The solution was stirred and allowed to reach room temperature slowly. After stirring for 5 h, the reaction mixture was filtered to remove the undesired impurities. Sodium iodide (439 mg, 2.93 mmol) and three drops of a concentrated solution of sodium metabisulfite was added to the filtrate. The resulting mixture was allowed to stir for 10 minutes, and it was extracted with chloroform (3×50 mL). The combined chloroform portion was dried ($Na_2SO_4$), evaporated in vacuo and crystallized with chloroform and hexane to yield (342 mg, 61%) of 1-methyl-3-[N-[β-[p-(3,3-pentan-1,5-diyl)triazen)-1-ylphenyl]ethyl]carbamoyl]pyridinium iodide (8): mp 146°–147° C.

In step 6, 1-methyl-3-[N-[β-(4-iodophenyl)ethyl]carbamoylpyridinium iodide (9) was prepared by using either precursor 7 or 8, as follows. Hydrochloric acid (HF, 48% solution, 0.044 mL) was dried by passing through a column (pasteur pipette) packed with anhydrous $MgSO_4$ (0.5 mL) which was eluted with acetone (3 mL). Sodium iodide, (25.5 mg, 0.17 mmol) was added and the solution was cooled to 0° C. A solution of 8 (40.8 mg, 0.085 mmol) or equivalent 7 in anhydrous acetone (1 mL) was added. The reaction mixture was stirred at room temperature for an hour and filtered. The filtrate was evaporated in vacuo. Water (5 mL) and chloroform (40 mL) was added to the residue, followed by the addition of sodium iodide (51 mg, 0.34 mmol) and a concentrated solution of sodium metabisulfite (3 drops). The reaction mixture was stirred at room temperature for 10 minutes. The organic layer was separated, and the aqueous layer was extracted with ethyl acetate (3×15 mL). The chloroform and ethyl acetate portions were combined and dried ($Na_2SO_4$). Evaporation of the solvent under vacuum gave 9 as a crude product in 67% yield (28.2 mg). An analytical sample was prepared by silica gel (SIL-B-200) column chromatography using methanol and chloroform (1:9) as the eluting solvent. Recrystallization from acetone gave pure (9): mp 214°–215° C.

In step 7, 1-methyl-3-[N-[β-(4-iodopheynyl)ethyl]-carbamoyl]-1,4-dihydropyridine (10) was prepared as follows. Sodium dithionite (68 mg, 0.39 mmol) was added with stirring to an argon flushed mixture of 9 (45 mg, 0.09 mmol), and sodium bicarbonate (58 mg, 0.69 mmol) in methanol (6 mL). Argon was bubbled through the reaction mixture during the entire course of this reaction. Water (~10 mL) was added dropwise until the reaction mixture became homogeneous. The solution was stirred vigorously for 10 minutes, $CHCl_3$, (45 mL) was added and the stirring was continued for an additional hour. The $CHCl_3$ layer was separated, the aqueous layer was extracted once with $CHCl_3$ (25 mL). The $CHCl_3$ portions were combined, dried ($Na_2SO_4$) and evaporated in vacuo to afford 10 as a syrup. Purification on a silica gel (SIL-B-200) column using 2.5% methanol in chloroform as the eluting solvent yielded 26 mg, 78%, pure 10 as syrup. Compound 10 was preserved under argon atmosphere to avoid air oxidation.

In step 8, a new synthesis of p-iodoaniline (12) was developed as a model for radioiodination. A solution of iodine (25.2 mg, 1.1 mmol) in methanol (1 mL) was added to a stirred suspension of 4-aminophenylmercuric acetate (70 mg, 0.2 mmol) in methanol (2 mL). The iodine color disappeared immediately. The mixture was stirred for 5 minutes and then diluted with water (15 mL) and extracted with ethyl ether. The ether portion was washed with an aqueous sodium bisulfite (10%) solution followed by water and dried ($Na_2SO_4$). Evaporation of ether gave iodoaniline which was found to be identical (mp 65° C., TLC, NMR) when compared with a commercial sample.

In step 9, 1-methyl-3-(p-iodophenyl)carbamoylpyridinium iodide (13) was prepared as follows. A solution of N-succinimidyl ester 4 (537 mg, 1.48 mmol) and p-iodoaniline (325 mg, 1.48 mmol) in DMF (6.0 mL) was stirred at room temperature for 5 h. The DMF was evaporated in vacuo and the residual syrup was triturated with methanol. The yellow crystalline product was collected by filtration and dried: yield 485 mg (71%); mp 247°–248° C.

In step 10, 1-methyl-3-[N-(4-iodopheynyl)]carbamoyl-1,4-dyhydropyridine (14) was prepared as follows. A suspension of 13 (40 mg, 86 μmol), sodium bicarbonate (55 mg, 0.65 mmol) and sodium dithionite (64 mg, 0.36 mmol) in methanol (5 mL) was saturated with argon which was bubbled through the reaction mixture continuously. The reaction mixture was stirred vigorously and water was added dropwise until the residue dissolved. Chloroform (15 mL) was added and the mixture stirred for 30 minutes. The mixture was diluted with water, the chloroform layer was separated and dried ($Na_2SO_4$). Evaporation of chloroform gave 25 mg (82%) of the desired product as a low melting solid.

Radiochemical Synthesis of [$^{125}I$]9 and [$^{125}I$]10

The [$^{125}I$]9 was prepared from the triazene substrates 7 or 8 as described above for unlabelled 9. The commercial Na[$^{125}I$] was neutralized with 48% HF solution, passed through a small column (pasteur pipette) packed with $MgSO_4$ (0.5 mL). Elution with acetone gave anhydrous radioiodide. A 2.5 mCi aliquot of anhydrous iodine-125 in acetone (1.25 mL) was added to a stirred cold (10±5° C.) solution of the triazene substrate 7 or 8 (1 equivalent) and NaI (2 equivalent) in acetone (0.5 mL). The reaction solution was stirred for 1 h, extracted with $CHCl_3$ and purified by silica gel column chromatography to give [$^{125}I$]8 (radiochemical yield 982 micro Ci, 39%). The product was identical with an unlabeled sample of 9 when examined on TLC (20% MeOH in $CHCl_3$). The [$^{125}I$]9 was reduced as described for the corresponding unlabeled compounds using $NaHCO_3$ and sodium dithionite to provide [$^{125}I$]10 in 38% radiochemical yield.

Radiochemical Synthesis of [$^{125}I$]12, [$^{125}I$]13 and [$^{125}I$]14

The commercial sample of iodine-125 (21.8 mCi) received in 0.1N NaOH was first neutralized with a hydrochloric acid (HF) solution. A solution of iodine (one atom equivalent of the substrate) in methanol (2 mL) was added to the radioiodide solution. The resulting solution was added to a cold (ice-water bath) stirred suspension of finely powdered 4-aminophenylmercuric acetate. An instantaneous reaction with iodine-color discharge was observed. The reaction mixture was stirred for 5 to 10 minutes, diluted with water (25 mL) and extracted with ethyl ether. The ether portion was washed with 10% aqueous sodium bisulfite solution followed by water and dried ($Na_2SO_4$). Evaporation of ether provided 4-[$^{125}I$]iodoaniline in 73% radiochemical yield. The [$^{125}I$]12 (15.8 mCi) and the succinimidyl ester 4 (27 mg, 0.075 mmol) were dissolved in DMF (1 mL). The solution was stirred for 4 h and purified by silica gel column chromatography to yield [$^{125}I$]13 (35.8% radiochemical yield). The [$^{125}I$]13 was reduced into [$^{125}I$]14 in an argon atmosphere, using $NaHCO_3$ and $Na_2S_2O_4$ as described for [$^{125}I$]10.

Rats were injected with the prepared compounds and the results of the brain imaging tests made on the injected rates are given in Tables 1, 2 and 3.

TABLE 1

The distribution of radioactivity in tissues of Sprague-Dawley rats following intravenous administration of the quaternary compound [$^{125}I$] (9) and of the dihydro compound [$^{125}I$] (10).[a]

| Compound | Time after Injection | Mean percent injected dose/gram (range) Tissue | | | | | | Brain: Blood (Mean) |
|---|---|---|---|---|---|---|---|---|
| | | Brain | Blood | Liver | Kidneys | Heart | Lungs | |
| [$^{125}I$]9 | 5 min | 0.03 | 0.39 | 8.03 | 16.46 | 0.25 | 0.47 | 0.08 |
| | | (0.02–0.03) | (0.34–0.48) | (6.76–10.44) | (13.02–19.07) | (0.24–0.29) | (0.44–0.56) | |
| | 15 min | 0.03 | 0.36 | 4.33 | 1.46 | 0.26 | 0.47 | 0.08 |
| | | (0.03–0.03) | (0.35–0.37) | (4.01–4.81) | (1.12–2.04) | (0.24–0.28) | (0.40–0.54) | |
| | 60 min | 0.02 | 0.27 | 0.93 | 0.56 | 0.20 | 0.32 | 0.07 |
| | | (0.02–0.03) | (0.25–0.32) | (0.75–1.14) | (0.48–0.72) | (0.19–0.23) | (0.30–0.36) | |
| [$^{125}I$]10 | 5 min | 1.03 | 0.42 | 3.09 | 3.70 | 3.60 | 4.04 | 2.44 |
| | | (0.94–1.18) | (0.39–0.44) | (2.75–3.32) | (3.03–4.74) | (3.35–4.02) | (3.67–4.46) | |
| | 30 min | 1.24 | 0.36 | 2.34 | 1.47 | 4.02 | 2.98 | 3.38 |
| | | (0.94–1.65) | (0.33–0.44) | (1.93–2.95) | (1.27–1.73) | (2.95–5.27) | (2.56–3.55) | |
| | 60 min | 0.96 | 0.29 | 1.66 | 1.20 | 2.89 | 2.19 | 3.22 |
| | | (0.89–1.04) | (0.27–0.31) | (1.43–1.99) | (1.05–1.33) | (2.29–3.14) | (0.41–3.03) | |

[a]Each animal (5 animals per time point) received either [$^{125}I$]9 or [$^{125}I$]10 by tail vein injection.
[$^{125}I$]10 shows steady retention and higher uptake in the brain as compared to [$^{125}I$]9.

TABLE 2

Distribution of radioactivity in tissues of Sprague-Dawley rats following intravenous administration of p-[$^{125}$I]iodoaniline conjugates of 1-methylpyridinium-3-carboxylate ([$^{125}$I]13) and the carrier, 1-methyl-1,4-dihydropyridine-3-carboxylate ([$^{125}$I]14).[a]

| Compound | Time after Injection | Mean percent injected dose/gram (range) Tissue | | | | | | Brain: Blood (Mean) |
|---|---|---|---|---|---|---|---|---|
| | | Brain | Blood | Liver | Kidneys | Heart | Lungs | |
| [$^{125}$I]13 | 5 min | 0.06 (0.05–0.07) | 1.11 (1.00–1.24) | 1.18 (1.03–1.31) | 2.10 (1.73–2.64) | 0.83 (0.79–0.85) | 0.84 (0.76–0.91) | 0.05 |
| | 15 min | 0.05 (0.03–0.06) | 0.87 (0.72–1.03) | 1.04 (0.81–1.18) | 0.74 (0.62–0.92) | 0.76 (0.68–0.84) | 0.72 (0.58–0.86) | 0.06 |
| | 30 min | 0.04 (0.03–0.06) | 0.75 (0.65–0.83) | 0.71 (0.54–0.89) | 0.65 (0.58–0.73) | 0.68 (0.58–0.82) | 0.62 (0.54–0.70) | 0.06 |
| | 60 min | 0.04 (0.03–0.06) | 0.67 (0.58–0.77) | 0.49 (0.38–0.57) | 0.53 (0.49–0.57) | 0.67 (0.58–0.75) | 0.57 (0.50–0.65) | 0.06 |
| [$^{125}$I]14 | 5 min | 1.14 (0.97–2.17) | 0.37 (0.28–0.46) | 1.65 (1.06–2.71) | 2.36 (1.64–3.43) | 2.86 (2.36–3.96) | 4.61 (3.62–7.08) | 3.87 |
| | 15 min | 1.16 (1.05–1.25) | 0.35 (0.31–0.40) | 1.56 (1.23–1.78) | 1.56 (1.42–1.82) | 2.43 (2.24–2.58) | 3.30 (3.10–3.77) | 3.29 |
| | 30 min | 1.01 (0.81–1.26) | 0.38 (0.35–0.40) | 1.18 (1.06–1.29) | 1.23 (1.14–1.40) | 2.18 (1.96–2.46) | 2.43 (2.26–2.89) | 2.66 |
| | 60 min | 1.12 (0.76–1.42) | 0.31 (0.28–0.37) | 0.82 (0.47–1.17) | 1.07 (0.89–1.19) | 1.88 (1.68–2.23) | 2.77 (2.11–3.79) | 3.6 |

[a] Each animal (5 animals per time point) received either [$^{125}$I]13 or [$^{125}$I]14 by tail vein injection
[$^{125}$I]14 shows steady retention and higher uptake in the brain as compared to [$^{125}$I]13.

TABLE 3

Distribution of radioactivity in tissues of Sprague-Dawley rats following intravenous administration of p-[$^{125}$I]iodoaniline [$^{125}$I]12[a]

| Time after Injection | Mean percent injected dose/gram (range) Tissue | | | | | |
|---|---|---|---|---|---|---|
| | Brain | Blood | Liver | Kidneys | Heart | Lungs |
| 5 min | 0.58 (0.35–0.72) | 0.94 (0.58–1.17) | 1.16 (0.73–1.45) | 0.97 (0.62–1.13) | 0.63 (0.39–0.74) | 0.86 (0.54–1.07) |
| 15 min | 0.43 (0.34–0.50) | 0.99 (0.95–1.06) | 1.57 (1.37–1.74) | 1.81 (1.59–2.03) | 0.57 (0.52–0.62) | 0.81 (0.77–0.86) |
| 30 min | 0.27 (0.18–0.36) | 0.77 (0.69–0.84) | 1.60 (1.57–1.66) | 1.80 (1.67–2.11) | 0.39 (0.36–0.42) | 0.62 (0.60–0.66) |
| 60 min | 0.06 (0.05–0.06) | 0.54 (0.49–0.58) | 1.60 (1.36–1.74) | 1.12 (0.99–1.24) | 0.24 (0.22–0.29) | 0.39 (0.36–0.44) |

[a] Each animal (5 animals per time point) received either [$^{125}$I]13 or [$^{125}$I]14 by tail vein injection These studies demonstrate that dihydropyridine-linked radioiodinated amines such as 1-methyl-3-[N-[β-(4-iodophenyl)ethyl]carbamoyl]1,4-dihydropyridine, [$^{125}$I], 10 and 1-methyl-3-N-(4-iodophenyl) carbamoyl-1,4-dihydropyridine, [$^{125}$I]14, readily cross the intact blood-brain barrier and show significantly higher brain uptake in rats compared to the corresponding quaternary pyridinium analogues [$^{125}$I]9 and [$^{125}$I]13. The studies also clearly demonstrate that radioiodinated p-iodoaniline when coupled to a dihydropyridine carrier (e.g., 14) shows significantly higher uptake and retention in the brain as compared to the parent [$^{125}$I]12. Apparently the lypophilic agents [$^{125}$I]10 and [$^{125}$I]14 cross the blood-brain barrier and are quaternized within the brain. The intact blood-brain barrier then prevents their release to allow high brain uptake. The oxidized quaternary form, however, being water soluble is washed out from the circulatory system to exhibit high brain:blood ratios. The nonlypophilic quaternary forms [$^{125}$I]9 and [$^{125}$I]13 do not cross the blood-brain barrier and therefore, do not show brain uptake. These studies have shown that brain-specific delivery of disclosed radiopharmaceuticals is possible and such agents and the technique can potentially be used for brain imaging in evaluation and detection of brain disease. The radioiodinated agents 10 and 14 also show good heart uptake, heart:blood ratios and retention in the heart (Tables 1 and 2) to suggest potential utility in the imaging of heart in addition to the brain.

In human applications the preferred radioisotope is iodine-123. The radiopharmaceutical synthesized with iodine-123 is combined with a saline solution or another suitable administering medium and is given to the subject by intravenous injection. Only a trace amount of the radiopharmaceutical is needed, the preferred amount being dependant on the extent of specific activity desired. Normally, one would want an amount sufficient to provide a distinct image, the exact amount depending on a number of factors that can be readily determined by persons skilled in the art. As seen by the Tables, uptake in rats is rapid, compounds 10 and 14 exhibiting 2.44 and 3.87 brain:blood ratios respectively after five minutes. Uptake is expected to be as rapid in humans with comparable brain:blood ratios meaning images could be recorded immediately after injection or sometime later as long as the brain:blood ratio of radioactivity is favorable. Since there are very few effective imaging agents available, this invention represents a considerable improvement in this field of technology.

We claim:

1. A compound comprising:
    a heterocyclic moiety wherein the hetero member of said heterocyclic moiety is nitrogen;
    said heterocyclic moiety being quaternary and capable of being reduced to a dihydrogenated form;
    said heterocyclic moiety having a carbonyl group attached to a carbon of the ring of said heterocyclic moiety;

said heterocyclic moiety being coupled at the carbonyl carbon with the amino nitrogen of an aromatic or aromatic alkyl amine;

said aromatic or aromatic alkyl amine having attached to a carbon of the aromatic ring a moiety that is readily replaced by a radiohalide selected from the group a substituted triazene, mercuric acetate and a boron moiety.

2. A compound of claim 1 wherein said heterocyclic moiety is selected from the group pyridine, quinoline, nicotine and pyrimidine.

3. A compound of claim 1 having the structure:

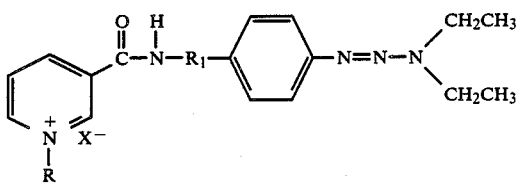

where

R = alkyl or aryl group
X = anion
$R_1$ = alkyl group.

4. A compound of claim 3 wherein R is $CH_3$, X is I, $R_1$ is $(CH_2)_2$.

5. A compound of claim 1 having the structure

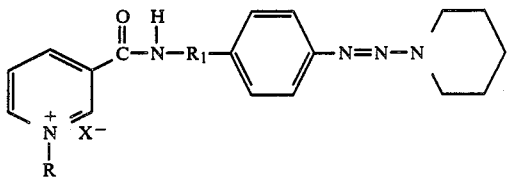

wherein
R = alkyl or aryl group
X = anion
$R_1$ = alkyl group.

6. A compound of claim 5 wherein R is $CH_3$, X is I, $R_1$ is $(CH_2)_2$.

* * * * *